US009088846B2

(12) United States Patent
Blanchard

(10) Patent No.: US 9,088,846 B2
(45) Date of Patent: *Jul. 21, 2015

(54) OVAL VARIABLE WALL EARBUD

(71) Applicant: Klipsch Group, Inc., Indianapolis, IN (US)

(72) Inventor: Mark A. Blanchard, Lebanon, IN (US)

(73) Assignee: Klipsch Group, Inc., Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/966,734

(22) Filed: Aug. 14, 2013

(65) Prior Publication Data

US 2015/0049896 A1 Feb. 19, 2015

(51) Int. Cl.
*H04R 25/00* (2006.01)
*H04R 1/10* (2006.01)

(52) U.S. Cl.
CPC ............ *H04R 1/1016* (2013.01); *H04R 1/1083* (2013.01); *H04R 2460/11* (2013.01)

(58) Field of Classification Search
CPC .... H04R 1/1016; H04R 1/1083; H04R 25/65; H04R 25/652; H04R 25/656; H04R 2460/11; A61F 2011/085
USPC .................. 381/370, 374, 380; 181/130, 135; 128/864–865, 867
See application file for complete search history.

(56) References Cited

U.S. PATENT DOCUMENTS

| 177,253 | A | 5/1876 | Keats |
| 789,876 | A | 5/1905 | Pape |
| 1,556,775 | A | 10/1925 | Fensky |
| 2,246,737 | A | 6/1941 | Knudsen |
| 2,430,229 | A | 11/1947 | Kelsey |
| 2,487,038 | A | 11/1949 | Baum |
| 2,521,414 | A | 9/1950 | Schier |
| 2,719,523 | A | 10/1955 | Von Glerke |
| 2,987,584 | A | 6/1961 | Webber |
| 3,061,689 | A | 10/1962 | McCarrell et al. |
| 3,080,011 | A | 3/1963 | Henderson |
| D207,216 | S | 3/1967 | Geib |
| RE26,258 | E | 8/1967 | Martin |
| 3,414,685 | A | 12/1968 | Geib et al. |
| 3,415,246 | A | 12/1968 | Hill |
| 3,548,118 | A | 12/1970 | Hutchings |

(Continued)

FOREIGN PATENT DOCUMENTS

| EP | 0959773 B1 | 12/2003 |
| EP | 1578168 A3 | 9/2005 |

(Continued)

*Primary Examiner* — Matthew Eason
(74) *Attorney, Agent, or Firm* — Dean McConnell IP Law

(57) ABSTRACT

An ear tip is disclosed that comprises an annular flange having a first end tapering downwardly to a second end and having a non-circular lateral cross-section generally in the shape of an oval. The annular flange has a varying wall thickness from a first set of opposite sides of the annular flange to a second set of opposite sides of the annular flange. An inner body extends internally from the first end within a hollow interior defined by the annular flange toward the second end. An acoustic channel extends through the inner body, where the annular flange at least partially occludes an ear canal from ambient noise and creates at least a partial air seal in the ear canal and the acoustic channel is configured to allow the passage of sound into the ear canal when the inner body is connected with a sound source.

20 Claims, 3 Drawing Sheets

(56) References Cited

U.S. PATENT DOCUMENTS

| | | |
|---|---|---|
| 3,610,841 A | 10/1971 | Hutchings |
| 3,618,697 A | 11/1971 | Littmann |
| 3,692,958 A | 9/1972 | Dymoke |
| 3,865,998 A | 2/1975 | Weiss et al. |
| 3,993,879 A | 11/1976 | Larkin |
| 4,006,321 A | 2/1977 | Carlson |
| D245,202 S | 7/1977 | Asker |
| 4,039,765 A | 8/1977 | Tichy et al. |
| 4,122,841 A | 10/1978 | Rock et al. |
| 4,261,432 A | 4/1981 | Gunterman |
| D259,279 S | 5/1981 | Takeda |
| 4,325,453 A | 4/1982 | Moussette |
| 4,335,281 A | 6/1982 | Scott et al. |
| 4,347,911 A | 9/1982 | Bertagna et al. |
| 4,548,082 A | 10/1985 | Engebretson et al. |
| 4,677,675 A | 6/1987 | Killion et al. |
| 4,764,168 A | 8/1988 | Suh |
| D298,356 S | 11/1988 | Falco |
| 4,867,149 A | 9/1989 | Falco |
| 4,870,688 A | 9/1989 | Voroba et al. |
| 4,875,233 A | 10/1989 | Derhaag et al. |
| 4,913,259 A | 4/1990 | Packard |
| 4,936,411 A | 6/1990 | Leonard |
| 5,031,219 A | 7/1991 | Ward et al. |
| D330,761 S | 11/1992 | Falco |
| 5,188,123 A | 2/1993 | Gardner, Jr. |
| 5,201,007 A | 4/1993 | Ward et al. |
| 5,288,953 A | 2/1994 | Peart |
| 5,295,193 A | 3/1994 | Ono |
| 5,298,692 A | 3/1994 | Ikeda et al. |
| D353,379 S | 12/1994 | Nakamura et al. |
| 5,487,012 A | 1/1996 | Topholm et al. |
| 5,692,059 A | 11/1997 | Kruger |
| 5,712,453 A | 1/1998 | Bungardt et al. |
| 5,781,638 A | 7/1998 | Hosaka et al. |
| 5,824,968 A | 10/1998 | Packard et al. |
| D402,752 S | 12/1998 | Falco |
| 5,917,918 A | 6/1999 | Callahan |
| 5,957,136 A | 9/1999 | Magidson et al. |
| 5,979,589 A | 11/1999 | Aceti |
| D427,304 S | 6/2000 | Magidson et al. |
| 6,175,633 B1 | 1/2001 | Morrill et al. |
| 6,205,227 B1 | 3/2001 | Mahoney et al. |
| 6,253,871 B1 | 7/2001 | Aceti |
| 6,258,043 B1 | 7/2001 | Raviv et al. |
| 6,359,993 B2 | 3/2002 | Brimhall |
| D468,299 S | 1/2003 | Boesen |
| D468,721 S | 1/2003 | Nguyen |
| 6,513,621 B1 | 2/2003 | Destauriers et al. |
| 6,532,295 B1 | 3/2003 | Brimhall et al. |
| D473,652 S | 4/2003 | Darley et al. |
| 6,574,345 B1 | 6/2003 | Huang |
| 6,643,378 B2 | 11/2003 | Schumaier |
| 6,648,813 B2 | 11/2003 | Zilberman et al. |
| 6,688,421 B2 | 2/2004 | Dyer et al. |
| 6,695,093 B1 | 2/2004 | Falco |
| 6,751,327 B1 | 6/2004 | Urso et al. |
| D499,397 S | 12/2004 | Hlas et al. |
| 6,920,228 B2 | 7/2005 | Redmer et al. |
| 6,920,229 B2 | 7/2005 | Boesen |
| 6,940,988 B1 | 9/2005 | Shennib et al. |
| D517,054 S | 3/2006 | Yang |
| 7,010,137 B1 | 3/2006 | Leedom et al. |
| 7,072,476 B2 | 7/2006 | White et al. |
| 7,079,662 B2 | 7/2006 | Niederdränk |
| 7,082,206 B2 | 7/2006 | Mahoney et al. |
| 7,092,543 B1 | 8/2006 | Mahoney et al. |
| 7,107,993 B2 | 9/2006 | Magidson |
| 7,123,733 B1 | 10/2006 | Borowsky et al. |
| D535,644 S | 1/2007 | Drambarean et al. |
| 7,185,655 B1 | 3/2007 | Redon |
| D542,773 S | 5/2007 | Drambarean et al. |
| 7,221,768 B2 | 5/2007 | Sjursen et al. |
| D549,222 S | 8/2007 | Huang |
| D550,201 S | 9/2007 | Drambarean et al. |
| D550,567 S | 9/2007 | Söderström |
| D550,655 S | 9/2007 | Falco |
| 7,314,047 B2 | 1/2008 | Falco |
| D563,945 S | 3/2008 | Johns et al. |
| D565,022 S | 3/2008 | Belliveau et al. |
| D567,217 S | 4/2008 | Kamo et al. |
| D569,842 S | 5/2008 | Yang |
| D575,767 S | 8/2008 | Lee |
| D575,773 S | 8/2008 | Yanai |
| D579,006 S | 10/2008 | Kim et al. |
| 2002/0058881 A1 | 5/2002 | Raviv et al. |
| 2002/0076057 A1 | 6/2002 | Voix |
| 2003/0159878 A1 | 8/2003 | Hakansson et al. |
| 2003/0172938 A1 | 9/2003 | Falco |
| 2004/0047481 A1 | 3/2004 | Bauman |
| 2004/0240691 A1 | 12/2004 | Grafenberg |
| 2005/0018838 A1 | 1/2005 | Meunier et al. |
| 2005/0111687 A1 | 5/2005 | Lederer |
| 2005/0165460 A1 | 7/2005 | Erfan |
| 2006/0050912 A1 | 3/2006 | Kidd et al. |
| 2006/0050916 A1 | 3/2006 | Wehner |
| 2006/0147072 A1 | 7/2006 | Sodoma et al. |
| 2006/0159297 A1 | 7/2006 | Wirola et al. |
| 2008/0187159 A1* | 8/2008 | Blanchard .............. 381/328 |
| 2011/0268308 A1* | 11/2011 | Vasquez ................. 381/380 |

FOREIGN PATENT DOCUMENTS

| | | |
|---|---|---|
| EP | 1681904 A1 | 7/2006 |
| JP | 10023578 A | 1/1998 |
| JP | 2000210327 A | 8/2000 |
| WO | 9737593 A1 | 10/1997 |
| WO | 9904601 A1 | 1/1999 |
| WO | 0108443 A2 | 2/2001 |
| WO | 2004077924 A2 | 9/2004 |
| WO | 2005025268 A1 | 3/2005 |
| WO | 2005112503 A1 | 11/2005 |
| WO | 2006068772 A2 | 6/2006 |

\* cited by examiner

MAJOR AXIS

MINOR AXIS

MAJOR AXIS

MAJOR AXIS

OVAL VARIABLE WALL EARBUD

INTRODUCTION

The inventions disclosed and claimed herein are earbuds that come in contact with the ear canal wall, adapted for use with earphones, stethoscopes, perytympanic hearing instruments (hearing aids), headsets, and ear plugs for hearing protection, and more particularly "in ear" applications. The devices to which the ear tips can be operatively attached are generally known in the art, including earphones that can be positioned on the head or over the ear, in the ear and wires capable of operatively connecting the ear tip to an audio source such as an analog or digital audio player. Alternative uses include operative attachment to stethoscopes, hearing aids, headsets, and as ear plugs.

DETAILED DESCRIPTION OF REPRESENTATIVE EMBODIMENTS

Figure 1:
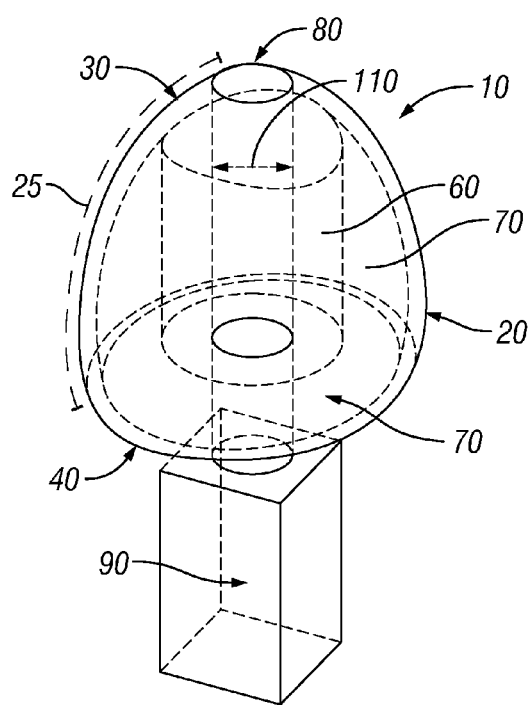
FIG. 1 shows a perspective view of one embodiment of an earbud.

For the purpose of promoting an understanding of the principles of the invention, reference is now made to the embodiments illustrated in the drawings and specific language is used to describe the same. No limitation of the scope of the invention is intended. Alterations and modifications to the illustrated devices, and other applications of the principles of the invention as illustrated herein are contemplated as would normally occur to one skilled in the art to which the invention relates.

Figure 2:
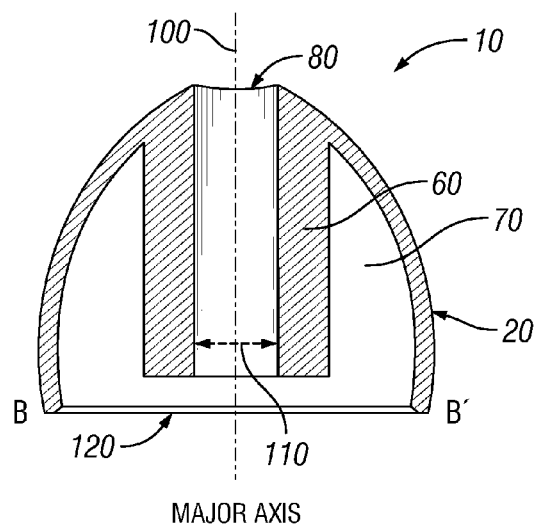
FIG. 2. shows a longitudinal cross-section of the earbud shown in FIG. 1 taken along the major axis.
Figure 3:
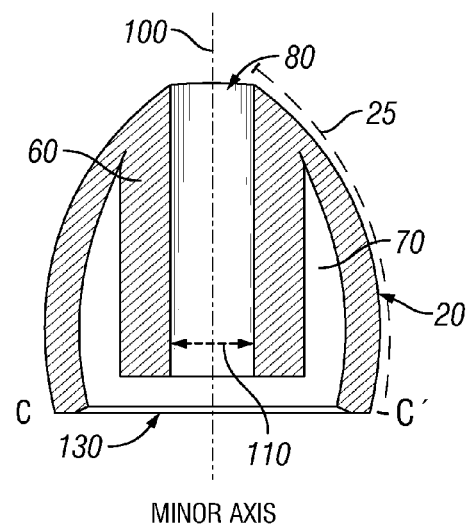
FIG. 3 shows a longitudinal cross-section of the earbud shown in FIG. 1 taken along the minor axis.

As shown in FIGS. 1 and 2, the earbud 10 has an annular flange 20 having a first or upper end 30, a second or lower end 40, at least a partially non-circular cross section 50 (shown for example in FIGS. 2 and 3). An inner body 60 extends from the first end 30 toward the second end 40 within a chamber 70 defined by the annular flange 20. An acoustic channel 80 extends through the inner body 60 to connect operatively the sound source or transducer 90 to the ear drum (not shown).

An inner body 60 is formed as part of the flange 20. The inner body 60 is positioned so that its longitudinal axis is generally concentric with the longitudinal axis of the flange 20 (i.e. along axis 100 as shown on FIGS. 2 and 3). The acoustic channel 80 extends through the inner body 60 and the first end 30. A transducer (not shown) may be positioned within the chamber 70 such that a portion of the transducer 90 is positioned within the acoustic channel 80 defined by the inner body 60. The inner body 60 may be formed integrally with the flange 20 or as a separate piece which is then attached to the flange 20.

The inner diameter 110 of the acoustic channel 80 is sized to secure an acoustic connection from a sound source or transducer 90. The acoustic channel 80 in one version has a diameter of about 1.26 millimeters. In another version, the acoustic channel 80 has a diameter of about 1.40 millimeters. Variations to the diameter of the acoustic channel 80 can be made without varying from the scope of the invention disclosed and claimed herein.

The exterior surface 25 of the flange 20 tapers upwardly from the second end 40 from the first end 30. The arc of the taper can be constant or variable. In one version the radius is 5 millimeters. In another version, the radius is 9 millimeters. In other embodiments, the flange 20 has a generally oval three-dimensional shape. Again, variations in the arc or radius of the taper can be made without varying from the scope of the invention disclosed and claimed herein.

Referring to FIGS. 2 and 3, the earbud 10 has a major axis 120 along B-B' and minor axis 130 along C-C'. The major axis 120 is longer than the minor axis 130. The minor axis 130 has a length from about 6 millimeters to about 10 millimeters. The major axis 120 has a length from about 9 millimeters to about 15 millimeters. The ratio of the length of the major axis 120 relative to the minor axis 130 can range from about 1.1:1 to about 3:1. The lengths of the axes can be varied without departing from the scope of the inventions disclosed and claimed herein.

Figure 4:
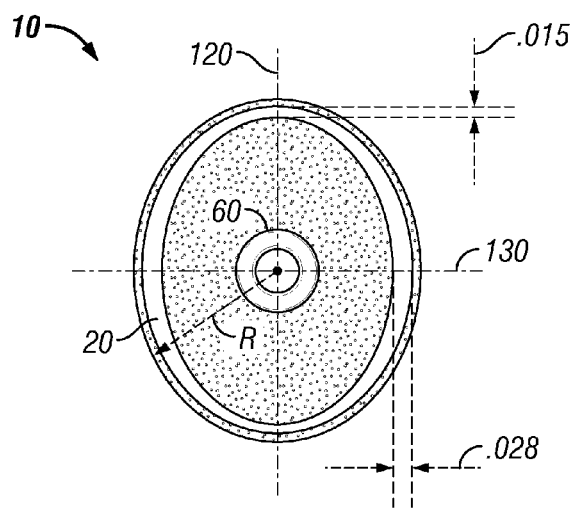
FIG. 4 shows a bottom view of the earbud shown in FIG. 1.

As illustrated in FIGS. 2 and 3, the width of the flange 20 varies from the major axis 120 to the minor axis 130. In particular, as the flange 20 transitions from the major axis 120 to the minor axis 130, the flange 20 becomes thicker. Referring to FIG. 4, a bottom view of the earbud 10 is illustrated that demonstrates how the flange 20 has a varying thickness. As depicted, at the minor axis 130 both sides of the flange 20 has a thickness of about 28 millimeters. As both sides of the flange 20 transition toward the major axis 120, the thickness of the flange 20 gets narrower. In the illustrated form, the thickness of the flange is approximately 15 millimeters at the major axis 120. The flange 20 therefore varies in thickness from the minor axis 130 to the major axis 120. In particular, the flange 20 decreases in thickness as it tapers from the minor axis 130 to the major axis 120. The varying flange 20 thickness allows the earbud 10 to more readily adapt to the inner ear when worn by a user. In one form, the thickness of the flange 20 varies from the minor axis 120 to the major axis 130 at a ration of about 2 to 1.

Figure 5:
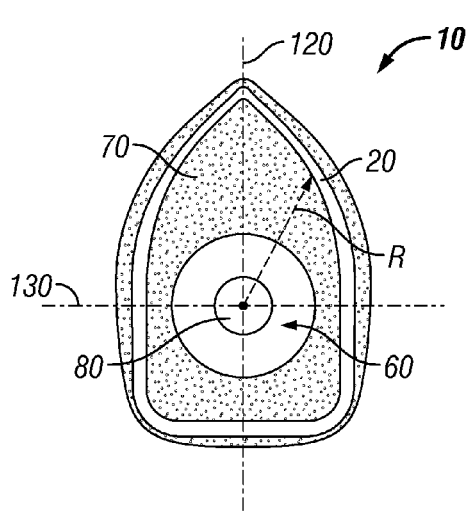
FIG. 5 shows a lateral cross-section of an embodiment having a generally triangular cross-section.
Figure 6:
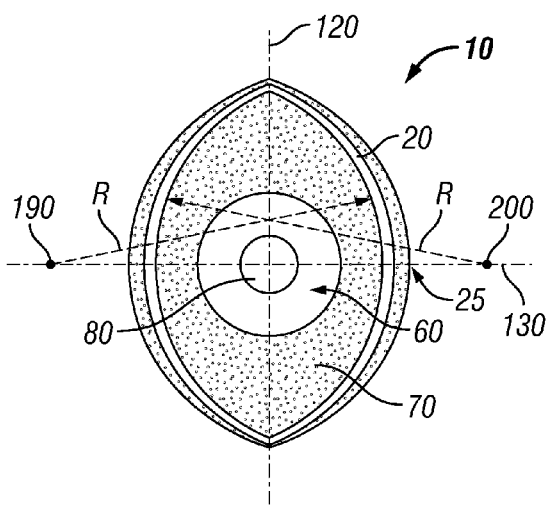
FIG. 6 shows a lateral cross-section of an embodiment having a clamshell shaped cross-section.

FIGS. 4-6 show several embodiments having different shaped lateral cross-sections. FIG. 4 shows a flange 20 having a generally elliptical or oval cross-section 50. The major axis 120 and minor axis 130 are shown. Radius "R" will decrease as it arcs from the major axis 120 to the minor axis 130 according to known mathematical equations for ellipses [$(x^2/a^2)+(y^2/b^2)=1$]. One can infinitely vary the radius "R" or the generally elliptical shape of the inventions without departing from the scope thereof as disclosed and claimed.

FIG. 5 shows another embodiment with a flange 20 having a generally triangular shaped lateral cross-section. This generally triangular shaped lateral cross-section can also be referred to as a tri-oval shape. The inner body 60 defines an acoustic channel 80. Taken from the axis of the acoustic channel 80, radius R varies in length as it arcs from the minor axis 130 to the major axis 120. Sections of the cross-section can have generally non-radial lineal geometries in varying length (FIG. 5). Again, as set forth above, the thickness of the flange 20 varies as it transitions from the minor axis 130 to the major axis 120. In particular, the flange 20 is thicker at the minor axis 130 and gets smaller as it transitions to the major axis 120.

FIG. 6 shows another embodiment with a flange 20 having a generally clamshell shaped lateral cross-section. This clamshell shape can be described as taking a longitudinal cross-section along the major axis 120 thereby separating the flange 20 into two halves having radii "R" based on center points 190, 200 outside the acoustic channel 80. Alternatively the center points 190, 200 can be inside the chamber 70 or acoustic channel 80. Sections of the cross-section can have generally non-radial lineal geometries in varying length (FIG. 5). Again, as set forth above, the thickness of the flange 20 varies as it transitions from the minor axis 130 to the major axis 120. In particular, the flange 20 is thicker at the minor axis 130 and gets smaller as it transitions to the major axis 120.

Rigid, deformable, flexible, elastic or resilient materials provide flexibility in sizing the ear bud, comfort, audio quality and durability. In one embodiment, the flange is a polymer. In another embodiment, the flange is an elastomeric polymer.

In single and multiple flange forms, the inner body 60 will have sufficient thickness and stiffness to resist deformation when it is connected to a sound source and when the earbud 10 is inserted into an ear.

Figure 7:
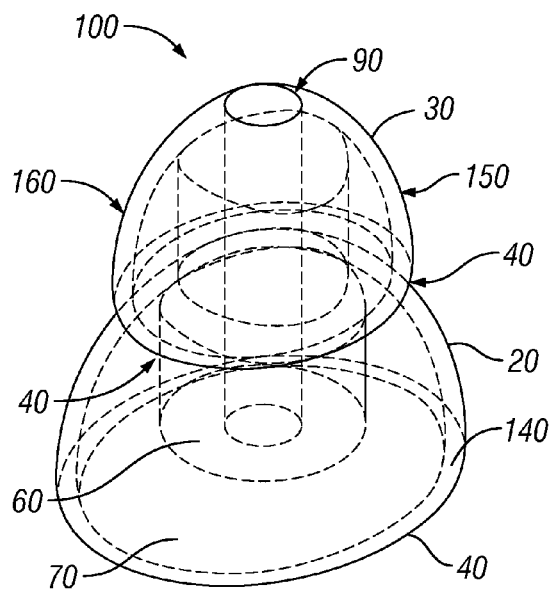
FIG. 7 shows a perspective view of another embodiment of the invention having two flanges.
Figure 8:
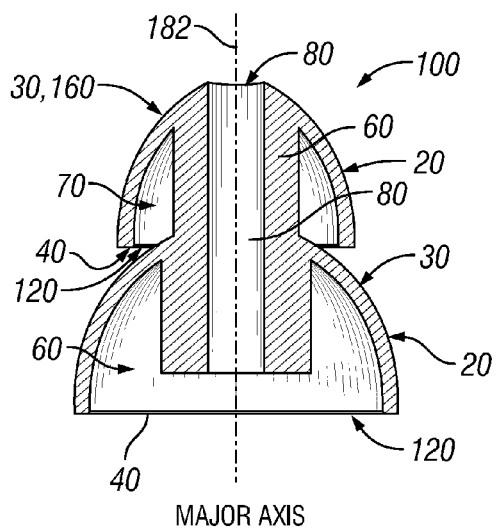
FIG. 8 shows a longitudinal cross-section of the embodiment shown in FIG. 7 taken along the major axis.
Figure 9:
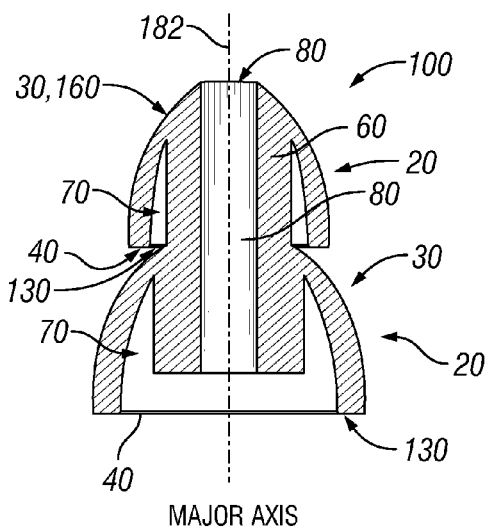
FIG. 9 shows a longitudinal cross-section of the embodiment shown in FIG. 7 taken along the minor axis.

Single flange earbuds 10 attenuate ambient noise by about 5 to about 15 dB. For additional noise isolation, multiple flanges 140, 150 can be used to yield attenuation up to about 32 dB. FIGS. 7-9 show a perspective view of double or stacked earbud 100 having a first flange 140 and a second flange 150 positioned along a common longitudinal axis 182. More than two flanges 140, 150 may be used without departing from the scope of the inventions disclosed and claimed. Again, as set forth above, the thickness of the flanges 20 varies as it transitions from the minor axis 130 to the major axis 120. In particular, the flange 20 is thicker at the minor axis 130 and gets smaller as it transitions to the major axis 120.

The flanges 140, 150 have generally decreasing diameters as the flanges 140, 150 transition to an insertable end 160. The insertable end 160 is that portion of the earbud 10 that is inserted the furthest into the ear canal. The flanges 140, 150 can be of single piece construction or multiple piece construction. For the embodiments having multiple flanges 140, 150, the inner body 60 can have an acoustic channel 80 extending through it. The inner body 60 traverses at least part of the length of both flanges 140, 150 as shown in FIG. 7-9. Each of the flanges 140, 150 has a first end 30 and a second end 40. At least one of the flanges 140, 150 has a partially non-circular cross section as described above with respect to the embodiment having a single flange 20. Each of the flanges 140, 150 defines a chamber 70.

While the use of words such as preferable, preferably, preferred or more preferred utilized in the description indicate that the feature so described may be more desirable, such feature(s) may not be necessary. Embodiments lacking the same are within the scope of the invention as defined by the claims that follow. In reading the claims, it is intended that when words such as "a," "an," "at least one," or "at least one portion" are used there is no intention to limit the claim to only one item unless specifically stated to the contrary in the claim. When the language "at least a portion" and/or "a portion" is used the item can include a portion and/or the entire item unless specifically stated to the contrary.

I claim:

1. An ear tip, comprising:
    an annular flange having an upper end and a lower end, where the flange has a non-circular lateral cross section running from approximately the upper end to the lower end, the non-circular lateral cross-section has a major axis and a minor axis, the major axis having a greater length than the minor axis, the flange tapering to the lower end from the upper end, wherein said flange has a greater thickness at said minor axis along said non-circular lateral cross-section than said major axis along said non-circular lateral cross-section, an inner body extending internally from the first end within a hollow interior defined by the flange toward the second end, and an acoustic channel extending through the inner body, where the flange at least partially occludes an ear canal from ambient noise and creates at least a partial air seal in the ear canal and the acoustic channel is configured to allow the passage of sound into the ear canal when the inner body is connected with a sound source.

2. The ear tip of claim 1 wherein said thickness of said minor axis tapers narrower as said annular flange approaches said major axis.

3. The ear tip of claim 2, wherein said minor axis tapers narrower at a ratio of about 2 to 1 to said major axis.

4. The ear tip of claim 3, wherein said minor axis has a width of about 28 millimeters and said major axis has a width of about 15 millimeters.

5. The ear tip of claim 1 wherein the ratio of the greater length of the major axis to the minor axis is from about 1.1:1 to about 3:1.

6. The ear tip of claim 1 wherein the cross-section has at least one substantially uniform arc as it extends from the minor axis to the major axis.

7. The ear tip of claim 1 wherein the cross-section has at least one variable arc as it extends from the minor axis to the major axis.

8. The ear tip of claim 1 wherein the cross-section has at least one generally increasing radius as it extends from the minor axis to the major axis.

9. The ear tip of claim 1 where the cross-section is oval.

10. The ear tip of claim 1 wherein the cross-section is generally triangular shaped.

11. The ear tip of claim 1 wherein the flange comprises a substantially rigid material.

12. The ear tip of claim 1 wherein the flange comprises a flexible material.

13. The ear tip of claim 1 wherein the flange comprises a deformable material.

14. The ear tip of claim 1 wherein the flange comprises an elastic material.

15. The ear tip of claim 1 wherein the flange comprises a resilient material.

16. The ear tip of claim 1 wherein the acoustic channel is sized to accept an insert to attenuate ambient noise from entering the acoustic channel.

17. An ear tip, comprising:
    an annular flange having a first end tapering downwardly to a second end and having a non-circular lateral cross-section generally in the shape of an oval, wherein said annular flange has a varying wall thickness from a first set of opposite sides of said annular flange to a second set of opposite sides of said annular flange along corresponding points of said non-circular lateral cross-section of said annular flange, an inner body extending internally from the first end within a hollow interior defined by the annular flange toward the second end, and an acoustic channel extending through the inner body, where the annular flange at least partially occludes an ear canal from ambient noise and creates at least a partial air seal in the ear canal and the acoustic channel is configured to allow the passage of sound into the ear canal when the inner body is connected with a sound source.

18. The ear tip of claim 17 wherein said varying wall thickness gradually decreases from said first set of opposite sides of said annular flange to said second set of opposite sides of said annular flange.

19. The ear tip of claim 18, wherein said decreases from approximately 28 millimeters on said first set of opposite sides to approximately 15 millimeters on said second set of opposite sides of said annular flange.

20. An ear tip, comprising:
an annular flange having a first end tapering downwardly to a second end and having a non-circular lateral cross-section generally in the shape of an oval, wherein said annular flange has a varying wall thickness from a first set of opposite sides of said annular flange to a second set of opposite sides of said annular flange along corresponding points of said non-circular lateral cross-section of said annular flange, where the annular flange at least partially occludes an ear canal from ambient noise and creates at least a partial air seal in the ear canal and an acoustic channel is configured to allow the passage of sound into the ear canal when the inner body is connected with a sound source.

* * * * *